(12) United States Patent
Endo

(10) Patent No.: US 11,224,408 B2
(45) Date of Patent: Jan. 18, 2022

(54) ULTRASOUND DIAGNOSTIC APPARATUS AND METHOD FOR CONTROLLING ULTRASOUND DIAGNOSTIC APPARATUS

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 686 days.

(21) Appl. No.: 16/145,645

(22) Filed: Sep. 28, 2018

(65) Prior Publication Data

US 2019/0029647 A1 Jan. 31, 2019

Related U.S. Application Data

(63) Continuation of application No. PCT/JP2017/011680, filed on Mar. 23, 2017.

(30) Foreign Application Priority Data

Apr. 1, 2016 (JP) .............................. JP2016-074400

(51) Int. Cl.
*A61B 8/00* (2006.01)
*A61B 8/14* (2006.01)
(Continued)

(52) U.S. Cl.
CPC ................ *A61B 8/468* (2013.01); *A61B 8/14* (2013.01); *A61B 8/463* (2013.01); *A61B 8/469* (2013.01);
(Continued)

(58) Field of Classification Search
CPC ......... A61B 8/468; A61B 8/469; A61B 8/463; A61B 8/5292; A61B 8/54; A61B 8/14; G01S 7/52098
See application file for complete search history.

(56) References Cited

U.S. PATENT DOCUMENTS

2003/0026464 A1   2/2003   Kamiyama et al.
2013/0163838 A1   6/2013   Barr et al.
(Continued)

FOREIGN PATENT DOCUMENTS

JP   2005-287942 A   10/2005
JP   2006-167048 A   6/2006
(Continued)

OTHER PUBLICATIONS

Extended European Search Report, dated Mar. 14, 2019, for European Application No. 17774652.6.
(Continued)

*Primary Examiner* — Sanjay Cattungal
(74) *Attorney, Agent, or Firm* — Birch, Stewart, Kolasch & Birch, LLP

(57) ABSTRACT

An ultrasound diagnostic apparatus includes: an imaging unit that converts a received signal output from an ultrasound probe into an image to generate an ultrasound image; an input unit that is used by a user to input patient information; a memory unit that stores content of an examination for continuously examining a plurality of examination parts so as to be associated with the patient information; an examination situation determination unit that, in a case in which new patient information is input to the input unit during the continuous examination, determines whether the examination of all of the plurality of examination parts related to the content of the examination associated with the patient information has ended; and a tag giving unit that gives an examination interruption tag to the patient information in a case in which it is determined that the examination of all of the plurality of examination parts has not ended and gives an examination end tag to the patient information in a case in which it is determined that the
(Continued)

examination of all of the plurality of examination parts has ended.

19 Claims, 8 Drawing Sheets

(51) Int. Cl.
    *G01S 7/52*     (2006.01)
    *A61B 8/08*     (2006.01)

(52) U.S. Cl.
    CPC .............. *A61B 8/5292* (2013.01); *A61B 8/54* (2013.01); *G01S 7/52098* (2013.01)

(56) References Cited

U.S. PATENT DOCUMENTS

| | | | |
|---|---|---|---|
| 2015/0182191 A1* | 7/2015 | Caluser | A61B 8/5246 600/440 |
| 2018/0203581 A1* | 7/2018 | Takeda | G06F 3/0481 |

FOREIGN PATENT DOCUMENTS

| | | |
|---|---|---|
| JP | 2006-167288 A | 6/2006 |
| JP | 2006-271862 A | 10/2006 |
| JP | 2007-325777 A | 12/2007 |
| JP | 2008-104774 A | 5/2008 |
| JP | 5242023 B2 | 7/2013 |

OTHER PUBLICATIONS

International Preliminary Report on Patentability and English translation of the Written Opinion of the International Searching Authority (Forms PCT/IB/326, PCT/IB/373, and PCT/ISA/237) For International Application No. PCT/JP2017/011680, dated Oct. 11, 2018.

International Search Report (form PCT/ISA/210) for International Application No. PCT/JP2017/011680 dated May 16, 2017, with English Translation.

* cited by examiner

ULTRASOUND DIAGNOSTIC APPARATUS AND METHOD FOR CONTROLLING ULTRASOUND DIAGNOSTIC APPARATUS

CROSS-REFERENCE TO RELATED APPLICATIONS

This application is a Continuation of PCT International Application No. PCT/JP2017/011680 filed on Mar. 23, 2017, which claims priority under 35 U.S.C. § 119(a) to Japanese Patent Application No. 2016-074400 filed on Apr. 1, 2016. The above application is hereby expressly incorporated by reference, in its entirety, into the present application.

BACKGROUND OF THE INVENTION

1. Field of the Invention

The present invention relates to an ultrasound diagnostic apparatus and a method for controlling the ultrasound diagnostic apparatus, and more particularly, to an ultrasound diagnostic apparatus that does not require an operation of a user in a case in which an examination is interrupted.

2. Description of the Related Art

In the related art, an ultrasound diagnostic apparatus using an ultrasound image has been put to practical use in the medical field. In general, in this type of ultrasound diagnostic apparatus, an ultrasound probe provided with an array transducer scans the body of a patient with an ultrasound beam and receives ultrasound echoes from the patient and the received signal is electrically processed to generate an ultrasound image.

For example, a method which continuously examines a plurality of predetermined examination parts, such as an extended focused assessment with sonography for trauma (eFAST) examination, is performed in a case in which the ultrasound diagnostic apparatus is used to diagnose a patient. In a case in which the examination is interrupted during the continuous examination, there is a concern that examination data including, for example, an ultrasound image obtained by the examination will not be appropriately stored. For this reason, JP5242023B discloses an ultrasound image diagnostic apparatus that appropriately store examination data even in a case in which an examination is interrupted.

SUMMARY OF THE INVENTION

However, the user needs to operate the ultrasound image diagnostic apparatus to perform an interruption process in order to interrupt an examination using the ultrasound image diagnostic apparatus disclosed in JP5242023B and it takes a lot of time and effort to perform the interruption process. In particular, in a case in which a patient different from the patient who is being examined needs to be urgently examined, it is difficult to appropriately perform the interruption process.

The invention has been made in order to solve the problems of the related art and an object of the invention is to provide an ultrasound diagnostic apparatus and a method for controlling the ultrasound diagnostic apparatus that do not require an operation of a user in a case in which an examination is interrupted.

According to the invention, there is provided an ultrasound diagnostic apparatus comprising: an ultrasound probe; an imaging unit that transmits and receives an ultrasound beam to and from a patient using the ultrasound probe and converts a received signal output from the ultrasound probe into an image to generate an ultrasound image of an imaging part of the patient; an input unit that is used by a user to input patient information including information for specifying a patient; a memory unit that stores content of an examination for continuously examining a plurality of examination parts of the patient associated with the patient information; an examination situation determination unit that, in a case in which new patient information is input to the input unit during the continuous examination, determines whether the examination of all of the plurality of examination parts related to the content of the examination associated with the patient information has ended; and a tag giving unit that gives an examination interruption tag indicating that an examination has been interrupted to the patient information in a case in which the examination situation determination unit determines that the examination of all of the plurality of examination parts related to the content of the examination associated with the patient information has not ended and gives an examination end tag indicating that an examination has ended to the patient information in a case in which the examination situation determination unit determines that the examination of all of the plurality of examination parts related to the content of the examination associated with the patient information has ended.

Preferably, the ultrasound diagnostic apparatus further comprises an apparatus control unit that stores the content of the examination in the memory unit so as to be associated with the patient information, generates examination data including at least one ultrasound image generated from the imaging unit by continuously examining the plurality of examination parts, and stores the generated examination data in the memory unit.

The ultrasound diagnostic apparatus may further comprise a part determination unit that determines the imaging part of the patient on the basis of the ultrasound image generated by the imaging unit. The examination situation determination unit may determine whether the examination of all of the plurality of examination parts related to the content of the examination associated with the patient information has ended on the basis of a determination result of the part determination unit.

The tag giving unit may give the examination interruption tag to the examination data in a case in which the examination situation determination unit determines that the examination of all of the plurality of examination parts related to the content of the examination associated with the patient information has not ended and may give the examination end tag to the examination data in a case in which the examination situation determination unit determines that the examination of all of the plurality of examination parts related to the content of the examination associated with the patient information has ended. The apparatus control unit may store the examination data, to which the examination interruption tag has been given by the tag giving unit, as examination interruption data in the memory unit so as to be associated with the patient information in a case in which the examination situation determination unit determines that the examination of all of the plurality of examination parts related to the content of the examination associated with the patient information has not ended and may store the examination data, to which the examination end tag has been given by the tag giving unit, as examination end data in the memory unit so as to be associated with the patient information in a case in which the examination situation determination unit determines that the examination of all of the plurality of examination parts related to the content of the examination associated with the patient information has ended.

The ultrasound diagnostic apparatus may further comprise an examination resumption determination unit that determines whether the examination interruption data associated with the new patient information has been stored in the memory unit, determines whether to resume the interrupted continuous examination in a case in which it is determined that the examination interruption data associated with the new patient information has been stored in the memory unit, and determines to start a new continuous examination in a case in which the interrupted continuous examination is not resumed.

The tag giving unit may give the examination end tag to the examination interruption data associated with the new patient information in a case in which the examination resumption determination unit determines to start the new continuous examination, and the apparatus control unit may store the examination interruption data, to which the examination end tag has been given by the tag giving unit, as the examination end data in the memory unit.

The examination resumption determination unit may determine to resume the interrupted continuous examination in a case in which an examination interruption period from a time when the tag giving unit gives the examination interruption tag to the new patient information to a time when the new patient information is input to the input unit again is less than a preset threshold value and may determine to start a new continuous examination in a case in which the examination interruption period is equal to or greater than the preset threshold value.

The apparatus control unit may store the examination data, from which the ultrasound image that is not suitable for diagnosis has been removed, in the memory unit according to a determination result of the examination situation determination unit.

According to the invention, there is provided a method for controlling an ultrasound diagnostic apparatus. The method comprises: a step of transmitting and receiving an ultrasound beam to and from a patient using an ultrasound probe and converting a received signal output from the ultrasound probe into an image to generate an ultrasound image of an imaging part of the patient; a step of allowing a user to input patient information including information for specifying a patient; a step of storing content of an examination for continuously examining a plurality of examination parts of the patient so as to be associated with the patient information; a step of, in a case in which new patient information is input during the continuous examination, determining whether the examination of all of the plurality of examination parts related to the content of the examination associated with the patient information has ended; and a step of giving an examination interruption tag indicating that an examination has been interrupted to the patient information in a case in which it is determined that the examination of all of the plurality of examination parts related to the content of the examination associated with the patient information has not ended and giving an examination end tag indicating that an examination has ended to the patient information in a case in which it is determined that the examination of all of the plurality of examination parts related to the content of the examination associated with the patient information has ended.

DESCRIPTION OF THE PREFERRED EMBODIMENTS

Hereinafter, embodiments of the invention will be described with reference to the accompanying drawings.

Embodiment 1

Figure 1:
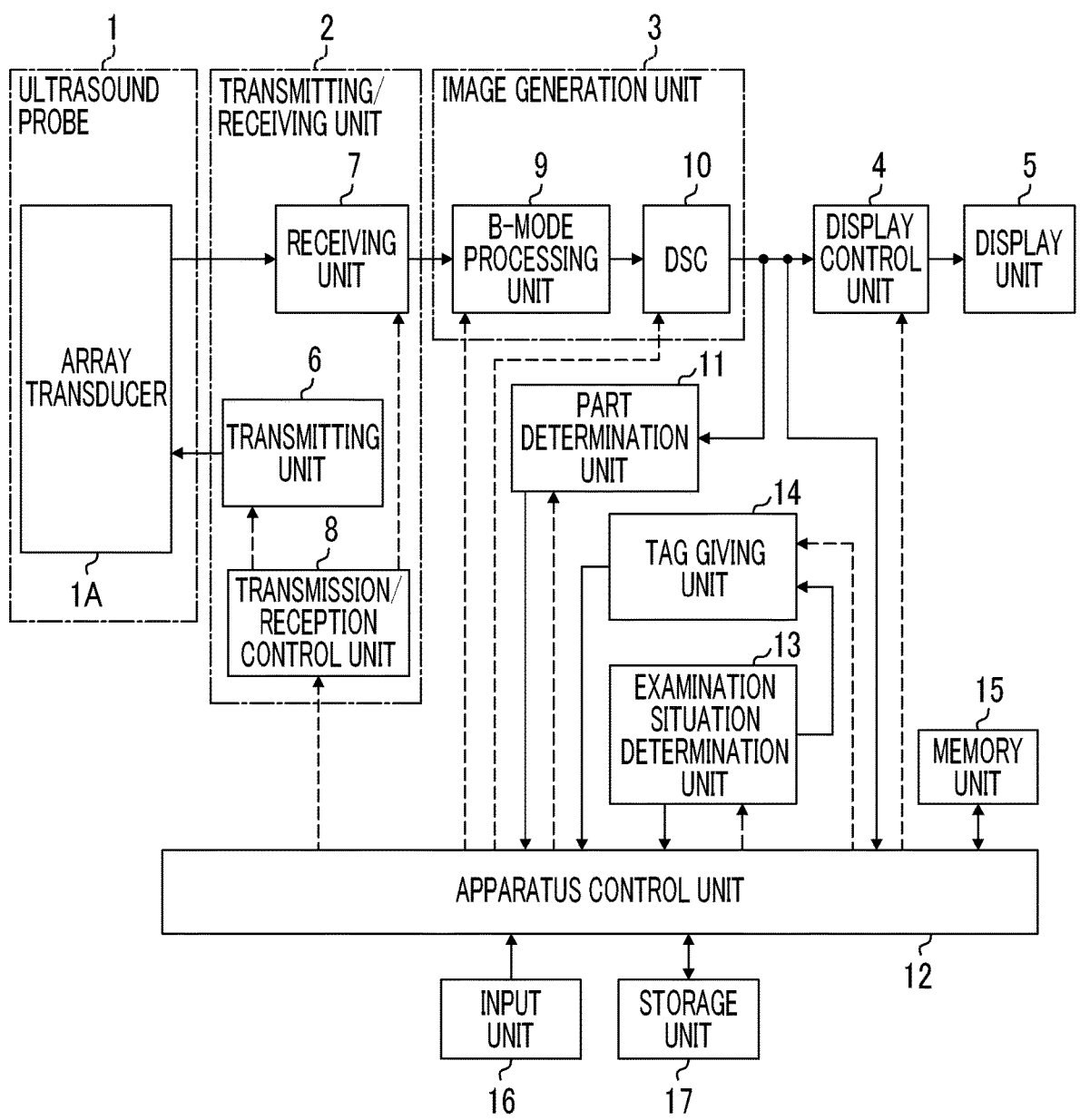
FIG. 1 is a block diagram illustrating the configuration of an ultrasound diagnostic apparatus according to Embodiment 1 of the invention.

FIG. 1 illustrates the configuration of an ultrasound diagnostic apparatus according to Embodiment 1 of the invention. The ultrasound diagnostic apparatus includes an ultrasound probe 1 provided with an array transducer 1A. An image generation unit 3 is connected to the ultrasound probe 1 through a transmitting/receiving unit 2 and a display unit 5 is connected to the image generation unit 3 through a display control unit 4.

The transmitting/receiving unit 2 includes a transmitting unit 6 and a receiving unit 7 that are connected to the array transducer 1A of the ultrasound probe 1 and a transmission/reception control unit 8 that is connected to the transmitting unit 6 and the receiving unit 7. The image generation unit 3 includes a brightness-mode (B-mode) processing unit 9 that is connected to the receiving unit 7 of the transmitting/receiving unit 2 and a digital scan converter (DSC) 10 that is connected to the B-mode processing unit 9. The display control unit 4 is connected to the DSC 10.

A part determination unit 11 and an apparatus control unit 12 are connected to the DSC 10 of the image generation unit 3.

The apparatus control unit 12 is connected to the transmission/reception control unit 8 of the transmitting/receiving unit 2, the B-mode processing unit 9 of the image generation unit 3, the display control unit 4, and the part determination unit 11. In addition, an examination situation determination unit 13 is connected to the apparatus control unit 12. A tag giving unit 14 is connected to the examination situation determination unit 13 and the apparatus control unit 12. Furthermore, a memory unit 15, an input unit 16, and a storage unit 17 are connected to the apparatus control unit 12.

The array transducer 1A of the ultrasound probe 1 includes a plurality of ultrasound transducers that are one-dimensionally or two-dimensionally arranged. Each of the ultrasound transducers transmits ultrasonic waves in response to a driving signal supplied from the transmitting unit 6. In addition, each of the ultrasound transducers receives ultrasound echoes from a patient and outputs a received signal. Each ultrasound transducer is, for example, a transducer in which electrodes are formed at both ends of a piezoelectric body made of piezoelectric ceramic typified by lead zirconate titanate (PZT), a polymer piezoelectric element typified by polyvinylidene difluoride (PVDF), or a piezoelectric crystal typified by lead magnesium niobate-lead titanate (PMN-PT).

In a case in which a pulsed voltage or a continuous-wave voltage is applied to the electrodes of the transducer, the piezoelectric body is expanded and contracted and pulsed or continuous ultrasonic waves are generated from each transducer. The ultrasonic waves are combined to form an ultrasound beam. In addition, each transducer receives propagated ultrasonic waves, is expanded and contracted, and generates an electric signal. The electric signal is output as a received ultrasound signal.

The transmitting/receiving unit 2 transmits and receives an ultrasound beam and the image generation unit 3 generates a B-mode image signal. Therefore, the transmitting/receiving unit 2 and the image generation unit 3 form an imaging unit. The transmitting unit 6 of the transmitting/receiving unit 2 includes, for example, a plurality of pulse generators, adjusts the amount of delay of each driving signal such that the ultrasonic waves transmitted from a plurality of ultrasound transducers in the array transducer 1A form an ultrasound beam, on the basis of a transmission delay pattern selected according to a control signal from the transmission/reception control unit 8, and supplies the driving signals to the plurality of ultrasound transducers.

Figure 2:
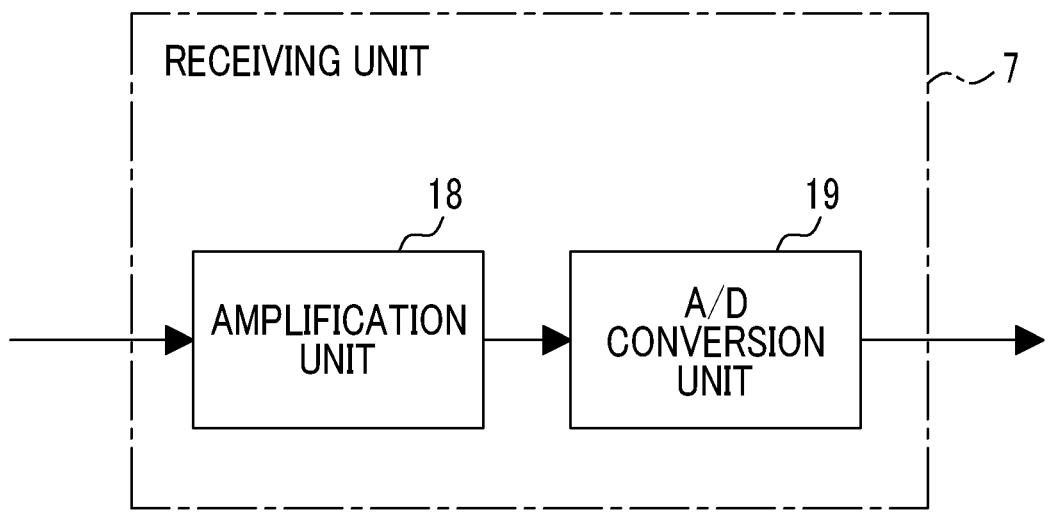
FIG. 2 is a block diagram illustrating the internal configuration of a receiving unit.

As illustrated in FIG. 2, the receiving unit 7 has a configuration in which an amplification unit 18 and an analogue/digital (A/D) conversion unit 19 are sequentially connected in series. The receiving unit 7 amplifies the received signals transmitted from each ultrasound transducer of the array transducer 1A with the amplification unit 18 and performs A/D conversion for the received signals with the A/D conversion unit 19 to generate digital received data.

The transmission/reception control unit 8 controls the transmitting unit 6 and the receiving unit 7 on the basis of various control signals transmitted from the apparatus control unit 12 such that the transmission of an ultrasound pulse to the patient and the reception of an ultrasound echo from the patient are repeated at a pulse repetition frequency (PRF) interval.

Figure 3:
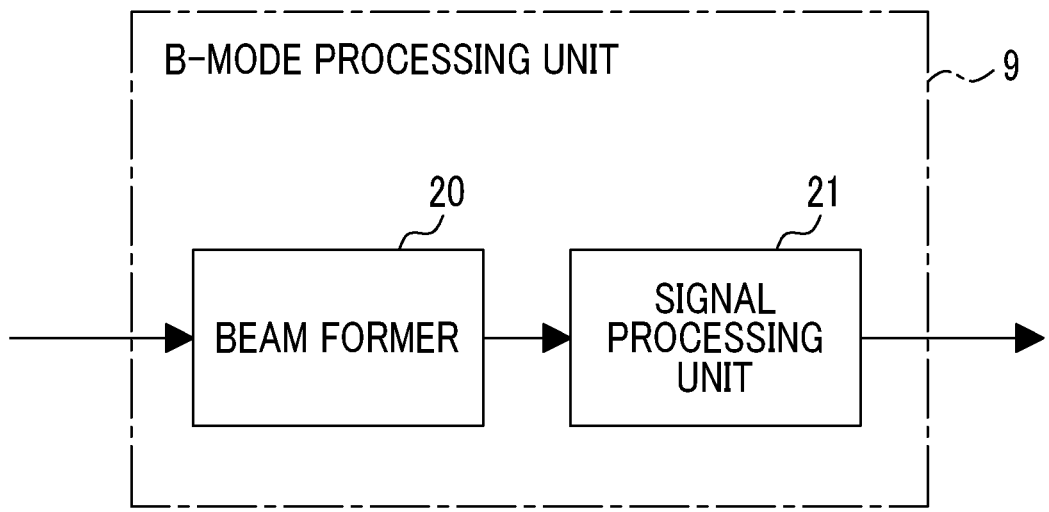
FIG. 3 is a block diagram illustrating the internal configuration of a B-mode processing unit.

The B-mode processing unit 9 of the image generation unit 3 has a configuration in which a beam former 20 and a signal processing unit 21 are sequentially connected in series, as illustrated in FIG. 3. The beam former 20 applies a delay to each received data item output from the receiving unit 7 of the transmitting/receiving unit 2 according to a sound speed or a sound speed distribution set on the basis of a reception delay pattern selected according to a control signal from the apparatus control unit 12 and adds the received data to perform a reception focusing process. A sound ray signal in which the focus of an ultrasound echo subjected to phasing addition is narrowed is generated by the reception focusing process.

The signal processing unit 21 corrects the attenuation of the sound ray signal generated by the beam former 20 depending on the vibration of the reflection position of ultrasonic waves and then performs an envelope detection process. In addition, the signal processing unit 21 performs various types of necessary image processing including a gradation process to generate a B-mode image signal which is tomographic image information related to the tissues of the patient.

The DSC 10 of the image generation unit 3 converts the B-mode image signal generated by the signal processing unit 21 into an image signal based on a general television signal scanning system (raster conversion).

The display control unit 4 displays a B-mode image on the display unit 5 on the basis of the B-mode image signal generated by the image generation unit 3.

The display unit 5 includes a display device, such as a liquid crystal display (LCD), and displays the B-mode image under the control of the display control unit 4.

The part determination unit 11 determines an imaging part of the patient on the basis of the B-mode image signal generated by the image generation unit 3.

Here, data including at least one B-mode image signal obtained by examining an examination part of the patient, the determination result of an imaging part of the patient by the part determination unit 11, and various kinds of information obtained by examination is defined as examination data. In addition, the examination data is configured such that a plurality of ultrasound images can be sequentially displayed and viewed as a motion picture.

In a case in which a continuous examination for continuously examining a plurality of predetermined examination parts in a predetermined order is performed, the plurality of examination parts and the examination order are defined as the content of the examination.

The memory unit 15 stores the content of various types of continuous examinations typified by an eFAST examination that continuously examines the examination parts in the order of, for example, the right abdomen, the left abdomen, the bladder, the heart, the right lung, and the left lung in advance. In addition, the memory unit 15 stores examination data obtained by examining the patient.

The memory unit 15 can be formed by a recording medium, such as a hard disk, a flexible disk, a magneto-optical disk (MO), a magnetic tape (MT), a random access memory (RAM), a compact disk read only memory (CD-ROM), a digital versatile disk read only memory (DVD-ROM), a secure digital card (SD card), a compact flash card (CF card), or a universal serial bus memory (USB memory). It is preferable that the memory unit 15 is formed by a server so as to store the examination data through a network. In this case, for example, the memory unit 15 can exchange the examination data with remote hospitals.

The storage unit 17 stores, for example, an operation program and can have the same configuration as the memory unit 15.

The input unit 16 is used by a user to perform an input operation and may include, for example, a keyboard, a mouse, a trackball, and a touch panel.

Here, identification symbols including information for specifying the patient, such as the name, sex, blood type, birth date, and phone number of the patient, are defined as patient information (patient specification information). An example of the patient information (patient specification information) is a patient identification (ID) number. The patient information (patient specification information) is input to the input unit 16 by an input operation of the user.

In a case in which the patient information (patient specification information) is input to the input unit 16, the apparatus control unit 12 associates the patient information (patient specification information) with the content of the examination for continuously examining a plurality of examination parts, such as the eFAST examination, stored in the memory unit 15 in advance. Then, the memory unit 15 stores the content of the examination associated with the patient information (patient specification information).

In addition, in a case in which new patient information (patient specification information) different from the patient information (patient specification information) of the patient who is currently being examined is input to the input unit 16, the apparatus control unit 12 outputs the new patient information (patient specification information) to the examination situation determination unit 13.

The apparatus control unit 12 generates examination data and stores the examination data in the memory unit 15.

In addition, the apparatus control unit 12 controls the transmission/reception control unit 8, the B-mode processing unit 9, the DSC 10, the display control unit 4, the part determination unit 11, the examination situation determination unit 13, and the tag giving unit 14 on the basis of commands input to the input unit 16 by the user.

In a case in which new patient information (patient specification information) different from the patient information (patient specification information) of the patient who is currently being examined is input to the input unit 16, the examination situation determination unit 13 reads the content of the examination associated with the patient information (patient specification information) from the memory unit 15 and automatically determines whether the examination of all of the examination parts related to the content of the examination associated with the patient information (patient specification information) has ended.

For example, in a case in which an eFAST examination for examining the right abdomen, the left abdomen, the bladder, the heart, the left lung, and the right lung is performed, the patient information (patient specification information) is associated with the content of the eFAST examination. Then, the examination situation determination unit 13 determines whether the examination of all of the examination parts has ended. Specifically, the examination situation determination unit 13 reads the examination data stored in the memory unit 15. In a case in which the read examination data includes the determination result of the part determination unit 11 indicating that all of the examination parts related to the content of the eFAST examination have been determined to be the imaging parts of the patient, the examination situation determination unit 13 determines that the examination of all of the examination parts related to the content of the eFAST examination has ended.

In a case in which the examination situation determination unit 13 determines that the examination of all of the plurality of examination parts related to the content of the examination associated with the patient information (patient specification information) has not ended, that is, the current examination has been interrupted, the tag giving unit 14 gives an examination interruption tag indicating that the examination has been interrupted to the patient information (patient specification information). In addition, the tag giving unit 14 gives the examination interruption tag to the examination data stored in the memory unit 15. The apparatus control unit 12 stores the examination data, to which the examination interruption tag has been given, as examination interruption data in the memory unit 15 so as to be associated with the patient information (patient specification information) to which the examination interruption tag has been given.

In addition, in a case in which the examination situation determination unit 13 determines that the examination of all of the plurality of examination parts related to the content of the examination associated with the patient information (patient specification information) has ended, that is, the current examination has ended, the tag giving unit 14 gives an examination end tag indicating that the examination has ended to the patient information (patient specification information). In addition, the tag giving unit 14 gives the examination end tag to the examination data stored in the memory unit 15. The apparatus control unit 12 stores the examination data, to which the examination end tag has been given, as examination end data in the memory unit 15 so as to be associated with the patient information (patient specification information) to which the examination end tag has been given.

The image generation unit 3, the display control unit 4, the transmission/reception control unit 8 of the transmitting/receiving unit 2, the part determination unit 11, the apparatus control unit 12, the examination situation determination unit 13, and the tag giving unit 14 are formed by a central processing unit (CPU) and an operation program that causes the CPU to perform various processes. However, these units may be formed by digital circuits. In addition, some or all of the image generation unit 3, the display control unit 4, the transmission/reception control unit 8 of the transmitting/receiving unit 2, the part determination unit 11, the apparatus control unit 12, the examination situation determination unit 13, and the tag giving unit 14 may be integrated into one CPU.

Next, the operation of Embodiment 1 will be described with reference to a flowchart illustrated in FIG. 4.

First, in Step S1, the user operates the input unit 16 to input the patient information (patient specification information) of the patient to be examined to the input unit 16. Here, the memory unit 15 stores the content of various types of continuous examinations typified by the eFAST examination that continuously examines, for example, the right abdomen, the left abdomen, the bladder, the heart, the right lung, and the left lung in this order in advance. In addition, the user operates the input unit 16 to select the type of continuous examination to be performed on the patient corresponding to the input patient information (patient specification information), for example, the eFAST examination. Then, the apparatus control unit 12 associates the content of the eFAST examination with the patient information (patient specification information) input to the input unit 16 and the memory unit 15 stores the content of the eFAST examination associated with the patient information (patient specification information).

In Step S2, the transmitting/receiving unit 2 performs the transmission and reception of ultrasound beams and scanning, using the plurality of ultrasound transducers in the array transducer 1A of the ultrasound probe 1. Each ultrasound transducer which has received ultrasound echoes from the patient outputs a received signal to the receiving unit 7. The receiving unit 7 performs amplification and A/D conversion for the received signal to generate received data.

In, Step S3, the received data is input to the image generation unit 3. The B-mode processing unit 9 performs the reception focusing process for the received data and the DSC 10 converts the received data into a signal to generate a B-mode image signal. The B-mode image signal is output from the image generation unit 3 to the display control unit 4 and a B-mode image is displayed on the display unit 5.

The B-mode image signal output from the DSC 10 of the image generation unit 3 is input to the part determination unit 11. In Step S4, the part determination unit 11 determines an imaging part of the patient. For example, in a case in which the right abdomen that is examined at the beginning of the eFAST examination is examined, a captured image of the right abdomen is included in the B-mode image signal and the part determination unit 11 determines that the imaging part of the patient is the right abdomen.

A known matching technique can be used to determine the imaging part of the patient on the basis of the B-mode image signal. In addition to the matching technique, for example, machine learning or a general image recognition method may be used to calculate similarity and the imaging part may be determined on the basis of the calculated similarity.

Here, the apparatus control unit 12 generates examination data including the B-mode image signal of the right abdomen output from the DSC 10 of the image generation unit 3, the determination result of the part determination unit 11 indicating that the imaging part of the patient is the right abdomen, and various kinds of information obtained by the examination. The B-mode image of the right abdomen is associated with the determination result of the part determination unit 11. In a case in which the user diagnoses the patient with the B-mode image, the user can refer to the determination result indicating that the imaging part of the patient is the right abdomen.

Then, the apparatus control unit 12 stores the examination data in the memory unit 15.

Then, in Steps S5 and S6, the B-mode image signal of the right abdomen is generated and the B-mode image of the right abdomen is displayed on the display unit 5. In addition, the B-mode image signal is added to the examination data. Then, in Step S7, it is determined whether new patient information (patient specification information) different from the patient information (patient specification information) of the patient who is currently being examined has been input to the input unit 16. In a case in which it is determined that the new patient information (patient specification information) has not been input to the input unit 16, it is determined whether the examination of the examination part that is being examined, that is, the right abdomen has ended in Step S8.

The user may operate the input unit 16 to determine whether the examination of the part that is being examined has ended. Alternatively, it may be automatically determined that the imaging part of the B-mode image signal has been changed from, for example, the right abdomen to the left abdomen and it may be determined whether the examination of the part that is being examined has ended. Specifically, in general, in a case in which the imaging part is changed, the probe is separated from the surface of the body and emits ultrasonic waves to the air. Therefore, it is possible to determine whether the imaging part has been changed by detecting the aerial emission state (a state in which a reflected signal is not obtained).

Until it is determined in Step S7 that new patient information (patient specification information) has been input to the input unit 16 or it is determined in Step S8 that the examination of the right abdomen that is being examined has ended, Steps S5 to S8 are repeated and the right abdomen is continuously diagnosed. In this way, various kinds of information including, for example, the B-mode image signal of the right abdomen and the diagnosis results of the user obtained by the examination are accumulated as the examination data.

Figure 5:
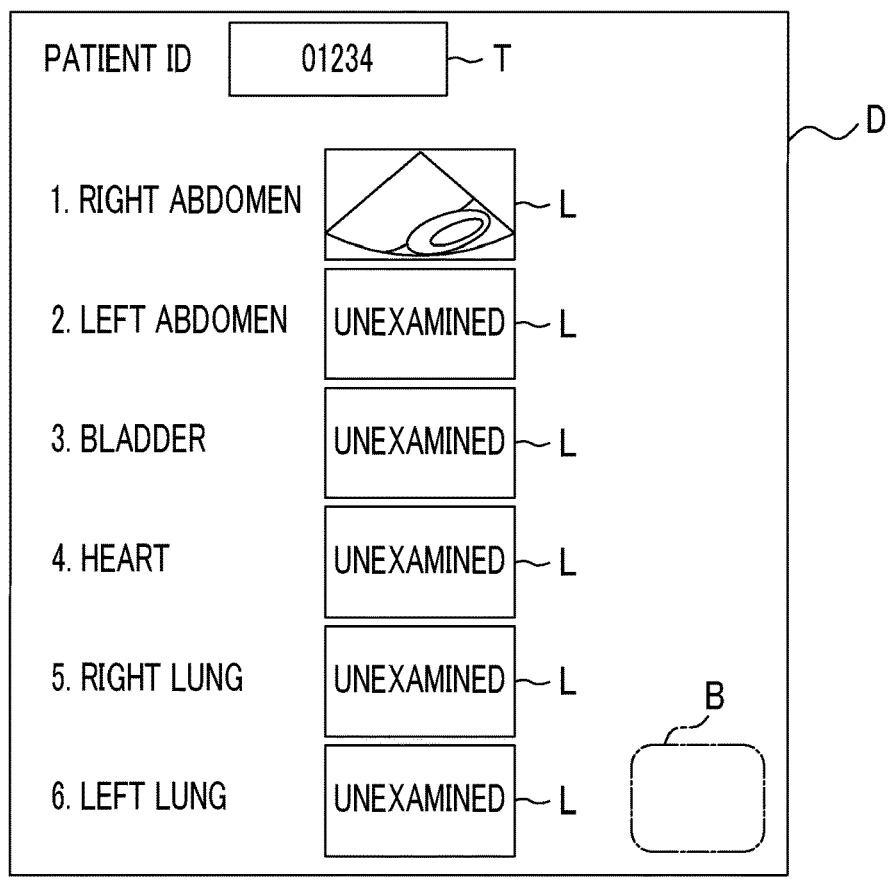
FIG. 5 is a diagram illustrating a dialogue displayed in Embodiment 1.

In a case in which it is determined in Step S8 that the examination of the right abdomen that is being examined has ended, the examination result is reflected in a dialogue D illustrated in FIG. 5. The dialogue D shows the situation of the continuous examination that is currently being performed and includes a text box T for inputting the patient information (patient specification information) and a plurality of situation display portions L indicating whether the examination of each examination part related to the continuous examination that is currently being performed has ended. In a case in which the corresponding examination parts have not been examined, "unexamined" is displayed in the plurality of situation display portions L. In a case in which the corresponding examination parts have been examined, ultrasound images corresponding to the examination parts are displayed in the plurality of situation display portions L.

The patient corresponding to the patient information (patient specification information) is specified by the patient information (patient specification information) input to the text box T and the examination situation of the patient are displayed in the dialogue D. As described above, the examination result indicating that the examination of the right abdomen has ended is reflected in the dialogue D in such a way that an ultrasound image of the right abdomen is displayed in the situation display portion L corresponding to the right abdomen.

In addition, the user can operate the input unit 16 such that the dialogue D and the B-mode image are displayed on the display unit 5. The user can operate the input unit 16 such that only the dialogue D or only the B-mode image is displayed on the display unit 5.

Then, in Step S9, it is determined whether the examination of all of the examination parts related to the content of the eFAST examination associated with the patient information (patient specification information) input to the input unit 16 has ended.

In a case in which it is determined in Step S9 that the examination of all of the examination parts related to the content of the eFAST examination associated with the patient information (patient specification information) input to the input unit 16 has not ended, the process returns to Step S2. For example, in a case in which the left abdomen is examined after the examination of the right abdomen ends, it is determined that the examination of all of the examination parts related to the content of the eFAST examination associated with the patient information (patient specification information) has not ended and the process returns to Step S2.

In Steps S2 and S3, a B-mode image signal of the left abdomen is generated. Then, in Step S4, the part determination unit 11 determines that the left abdomen captured in the B-mode image signal output from the DSC 10 of the image generation unit 3 is the imaging part of the patient. In Steps S5 and S6, a B-mode image signal of the left abdomen is generated. Then, the B-mode image signal of the left abdomen and the determination result indicating that the imaging part of the patient is the left abdomen are added to the examination data.

In this way, Steps S2 to S9 are repeated and the examination of a plurality of examination parts related to the content of the eFAST examination associated with the patient information (patient specification information) ends sequentially. The ultrasound images corresponding to each examination part are displayed in the plurality of situation display portions L of the dialogue D illustrated in FIG. 5.

In a case in which the ultrasound images are displayed in all of the situation display portions L, the user determines whether to end the examination in Step S9. Specifically, an icon for performing an end process is displayed in a blank B of the dialogue D. In a case in which the user selects the icon through the input unit 16, the examination is determined to end and the determination result is output from the apparatus control unit 12 to the tag giving unit 14. Then, in Step S11, the end process is performed. The end process is performed through a process in Steps S31 and S32 of the flowchart illustrated in FIG. 7.

In Step S31, first, the tag giving unit 14 that has received the determination result from the apparatus control unit 12 gives the examination end tag indicating that the examination has ended to the patient information (patient specification information). Then, the tag giving unit 14 gives the examination end tag to the examination data stored in the memory unit 15. Then, in Step S32, the apparatus control unit 12 stores the examination data, to which the examination end tag has been given, as the examination end data in the memory unit 15 so as to be associated with the patient information (patient specification information) to which the examination interruption tag has been given. In this way, the eFAST examination of the patient corresponding to the patient information (patient specification information) input to the input unit 16 ends.

Figure 6:
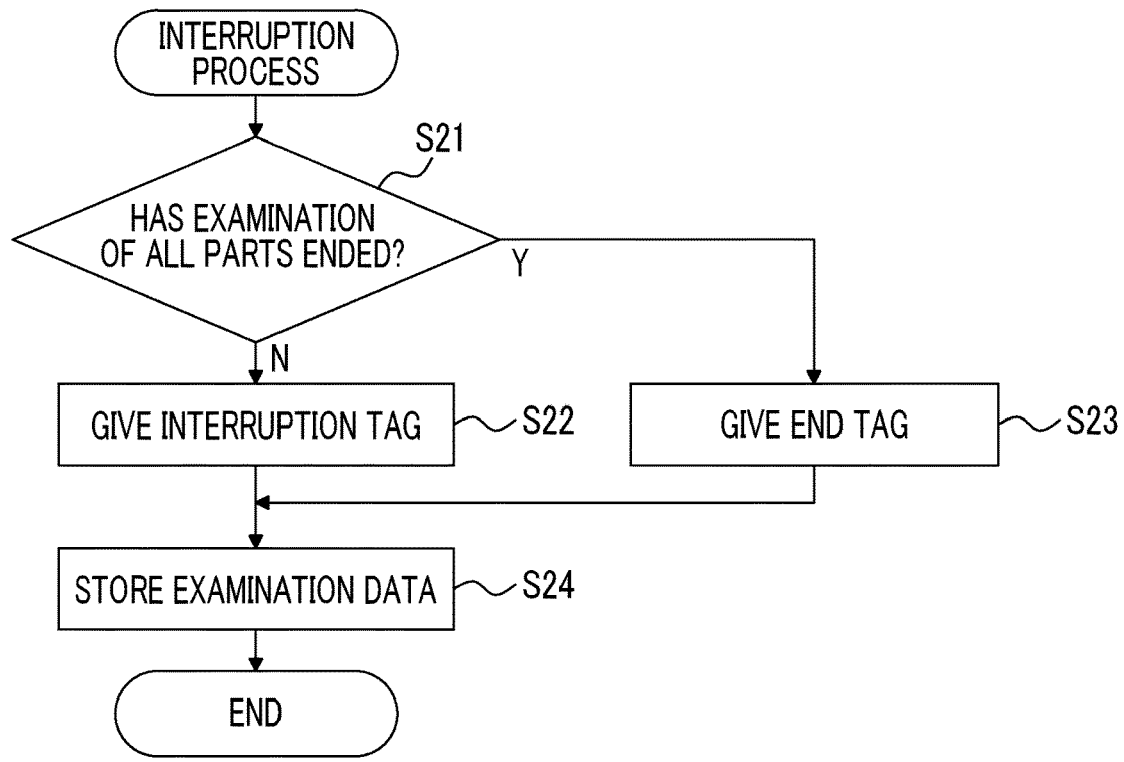
FIG. 6 is a flowchart illustrating an interruption process according to Embodiment 1.

On the other hand, in a case in which it is determined in Step S7 that new patient information (patient specification information) different from the patient information (patient specification information) of the patient who is currently being examined has been input to the text box T of the dialogue D illustrated in FIG. 5 through the input unit 16, an interruption process is performed in Step S10. The interruption process is performed through a process from Step S21 to Step S24 in a flowchart illustrated in FIG. 6.

First, in Step S21, it is automatically determined whether the examination of all of the examination parts related to the content of the eFAST examination associated with the patient information (patient specification information) of the patient who is currently being examined has ended. Specifically, the examination situation determination unit 13 reads the examination data stored in the memory unit 15 and determines whether the examination of all of the examination parts related to the content of the eFAST examination associated with the patient information (patient specification information) has ended on the basis of the determination result of the part determination unit 11 included in the read examination data.

In a case in which it is determined in Step S21 that the examination of all of the examination parts related to the content of the eFAST examination associated with the patient information (patient specification information) has not ended, the process proceeds to Step S22. For example, in a case in which the examination of only the right abdomen has ended, only the determination result indicating that the imaging part of the patient is the right abdomen is included in the read examination data. The examination situation determination unit 13 determines that the examination of all of the examination parts related to the content of the eFAST examination associated with the patient information (patient specification information) of the patient who is currently being examined has not ended, that is, the eFAST examination has been interrupted, on the basis of the determination result, and outputs the determination result to the tag giving unit 14.

Then, in Step S22, first, the tag giving unit 14 that has received the determination result from the examination situation determination unit 13 gives the examination interruption tag indicating that the examination has been interrupted to the patient information (patient specification information) of the patient who is currently being examined. Then, the tag giving unit 14 gives the examination interruption tag to the examination data stored in the memory unit 15.

Then, in Step S24, the apparatus control unit 12 stores the examination data, to which the examination interruption tag has been given, as the examination interruption data in the memory unit 15 so as to be associated with the patient information (patient specification information) to which the examination interruption tag has been given.

On the other hand, in Step S21, in a case in which the examination data read from the memory unit 15 by the examination situation determination unit 13 includes the determination result of the part determination unit 11 indicating that all of the examination parts related to the content of the eFAST examination are the imaging parts of the patient, the examination situation determination unit 13 determines that the examination of all of the examination parts related to the content of the eFAST examination associated with the patient information (patient specification information) of the patient who is currently being examined has ended and outputs the determination result to the tag giving unit 14.

Then, in Step S23, first, the tag giving unit 14 that has received the determination result from the examination situation determination unit 13 gives the examination end tag to the patient information (patient specification information) of the patient who is currently being examined. Then, the tag giving unit 14 gives the examination end tag to the examination data stored in the memory unit 15.

Then, in Step S24, the apparatus control unit 12 stores the examination data, to which the examination end tag has been given, as examination end data in the memory unit 15 so as to be associated with the patient information (patient specification information) to which the examination end tag has been given.

As such, in a case in which new patient information (patient specification information) different from the patient information (patient specification information) of the patient who is currently being examined is input to the input unit 16, it is determined whether the examination has been interrupted and the examination interruption data or the examination end data is automatically stored in the memory unit 15. Therefore, the user does not need to operate the input unit 16 in order to interrupt the examination. In addition, for example, in a case in which a patient different from the patient who is currently being examined is transported and the transported patient needs to be urgently examined, it is possible to appropriately store the examination data of the patient who has been examined so far.

Figure 4:
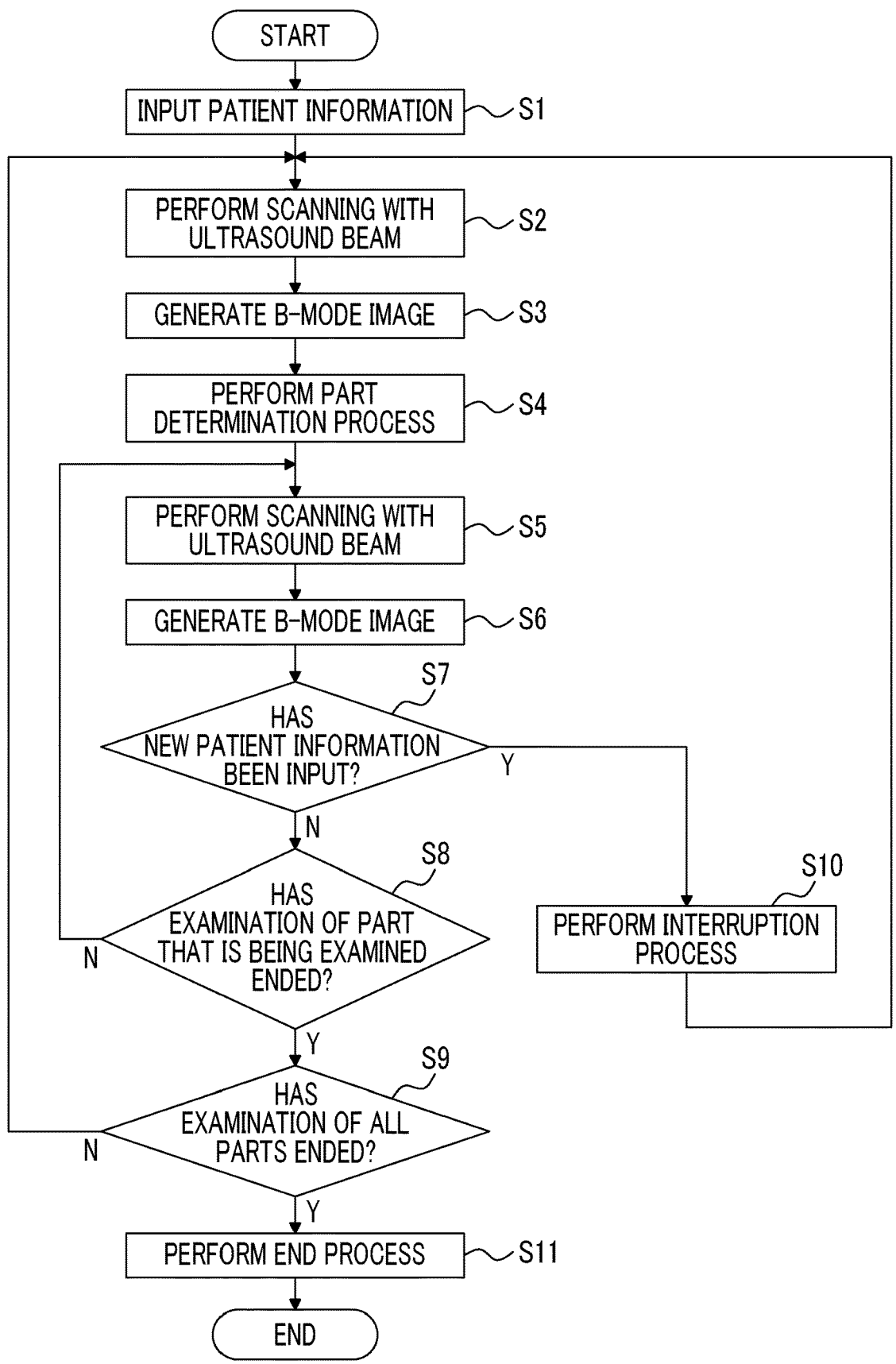
FIG. 4 is a flowchart illustrating the operation of Embodiment 1.

In a case in which the examination data of the patient who has been examined so far is stored in the memory unit 15 in Step S24, the process returns to Step S2 in the flowchart illustrated in FIG. 4 and a new examination of the patient corresponding to the new patient information (patient specification information) starts.

For example, in a case in which the eFAST examination is performed on a new patient corresponding to new patient information (patient specification information), Steps S2 to S9 are repeated and the examination of a plurality of examination parts related to the content of the eFAST examination associated with the new patient information (patient specification information) ends sequentially. The ultrasound images corresponding to each examination part are displayed in the plurality of situation display portions L of the dialogue D illustrated in FIG. 5.

In a case in which the ultrasound images are displayed in all of the situation display portions L, an icon for performing the end process is displayed in the blank B of the dialogue D in Step S9. In a case in which the user selects the icon through the input unit 16, the end process is performed in Step S11.

Figure 7:
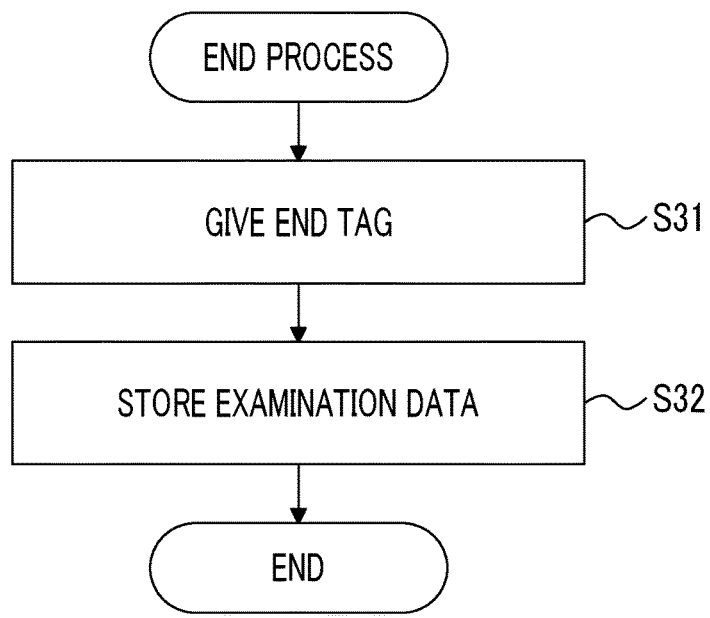
FIG. 7 is a flowchart illustrating an end process according to Embodiment 1.

In Step S31 of the flowchart illustrated in FIG. 7, first, the tag giving unit 14 gives the examination end tag to the new patient information (patient specification information). Then, the tag giving unit 14 gives the examination end tag to the examination data stored in the memory unit 15. Then, in Step S32, the apparatus control unit 12 stores the examination data, to which the examination end tag has been given, as the examination end data in the memory unit 15. In this way, the eFAST examination of the patient corresponding to the new patient information (patient specification information) input to the input unit 16 ends.

Figure 8:
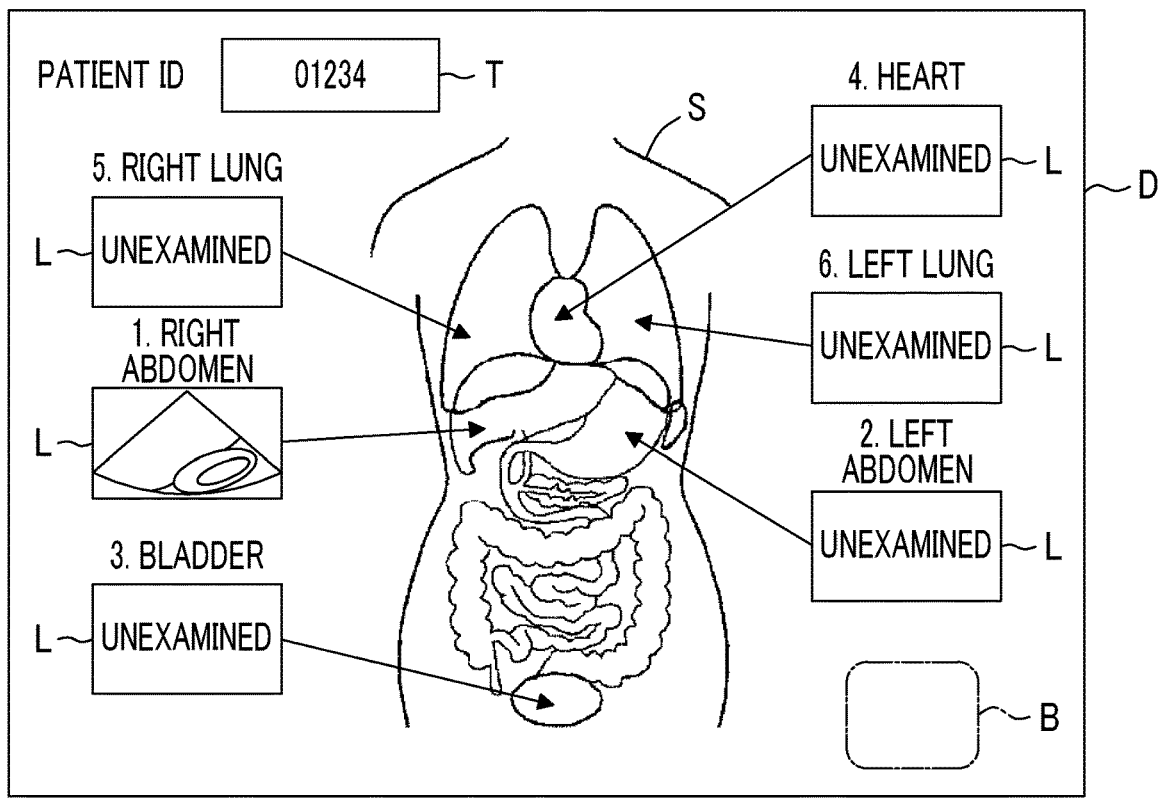
FIG. 8 is a diagram illustrating a dialogue displayed in a modification example of Embodiment 1.

As described above, the dialogue D illustrated in FIG. 5 includes the text box T and the plurality of examination situation display portions L. However, as illustrated in FIG. 8, the dialogue D may be configured such that a schema image S illustrating each examination part of the patient is added. The configuration in which the schema image S is added to the dialogue D makes it possible for the user to easily check, for example, the position of each examination part related to the content of the eFAST examination.

In addition, since the examination data is configured such that a plurality of ultrasound images accumulated by the examination are sequentially displayed and viewed as a motion picture, capacity is likely to increase. In some cases, the examination data includes a B-mode image that is not suitable for diagnosis, such as a B-mode image that is all black due to inappropriate contact between the ultrasound probe 1 and the patient, a B-mode image that is all white, or a B-mode image that includes a large amount of noise. It takes a lot of time and effort for the user to remove the B-mode image that is not suitable for diagnosis with the input unit 16.

For this reason, the apparatus control unit 12 can be configured so as to automatically remove the B-mode image that is not suitable for diagnosis from the examination data using, for example, the above-mentioned known matching technique. With this configuration, the apparatus control unit 12 automatically removes the B-mode image that is not suitable for diagnosis from the examination data before the tag giving unit 14 gives the examination interruption tag or the examination end tag to the examination data.

As such, since the apparatus control unit 12 automatically removes the B-mode image that is not suitable for diagnosis from the examination data, it is possible to easily prevent an increase in the capacity of the examination data stored in the memory unit 15.

Embodiment 2

In Embodiment 1, in a case in which new patient information (patient specification information) different from the patient information (patient specification information) of the patient who is currently being examined is input to the input unit 16, the interruption process is performed and then a new examination of a patient corresponding to the new patient information (patient specification information) starts. However, the invention is not limited thereto. In Embodiment 2, in a case in which the examination of the patient corresponding to the new patient information (patient specification information) was interrupted in the past, it is possible to resume the interrupted examination.

Figure 9:
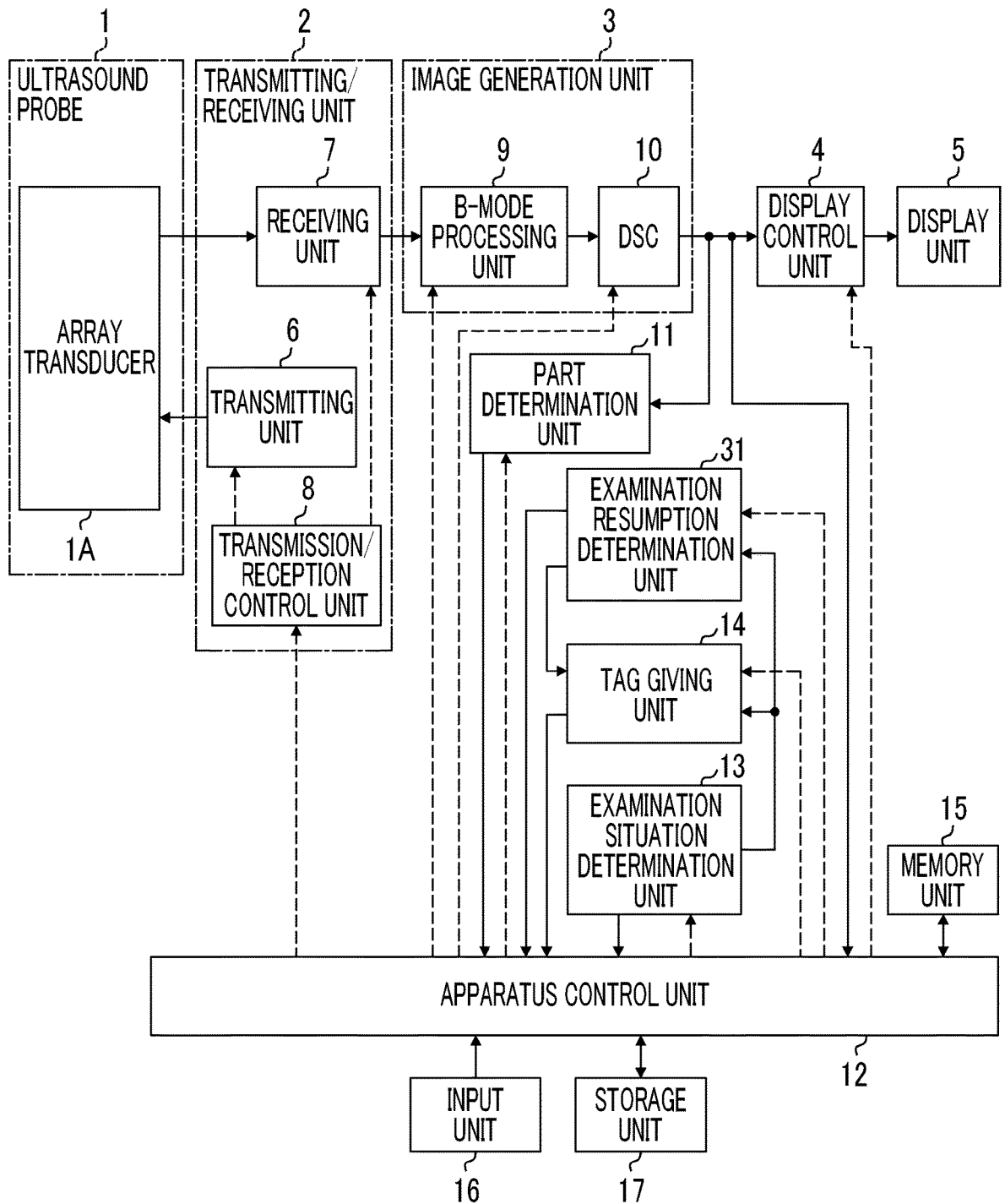
FIG. 9 is a block diagram illustrating the configuration of Embodiment 2.

FIG. 9 illustrates the configuration of an ultrasound diagnostic apparatus according to Embodiment 2. The ultrasound diagnostic apparatus according to Embodiment 2 has the same configuration as the ultrasound diagnostic apparatus according to Embodiment 1 illustrated in FIG. 1 except that it further includes an examination resumption determination unit 31. The examination resumption determination unit 31 is connected to the apparatus control unit 12, the examination situation determination unit 13, and the tag giving unit 14.

Figure 10:
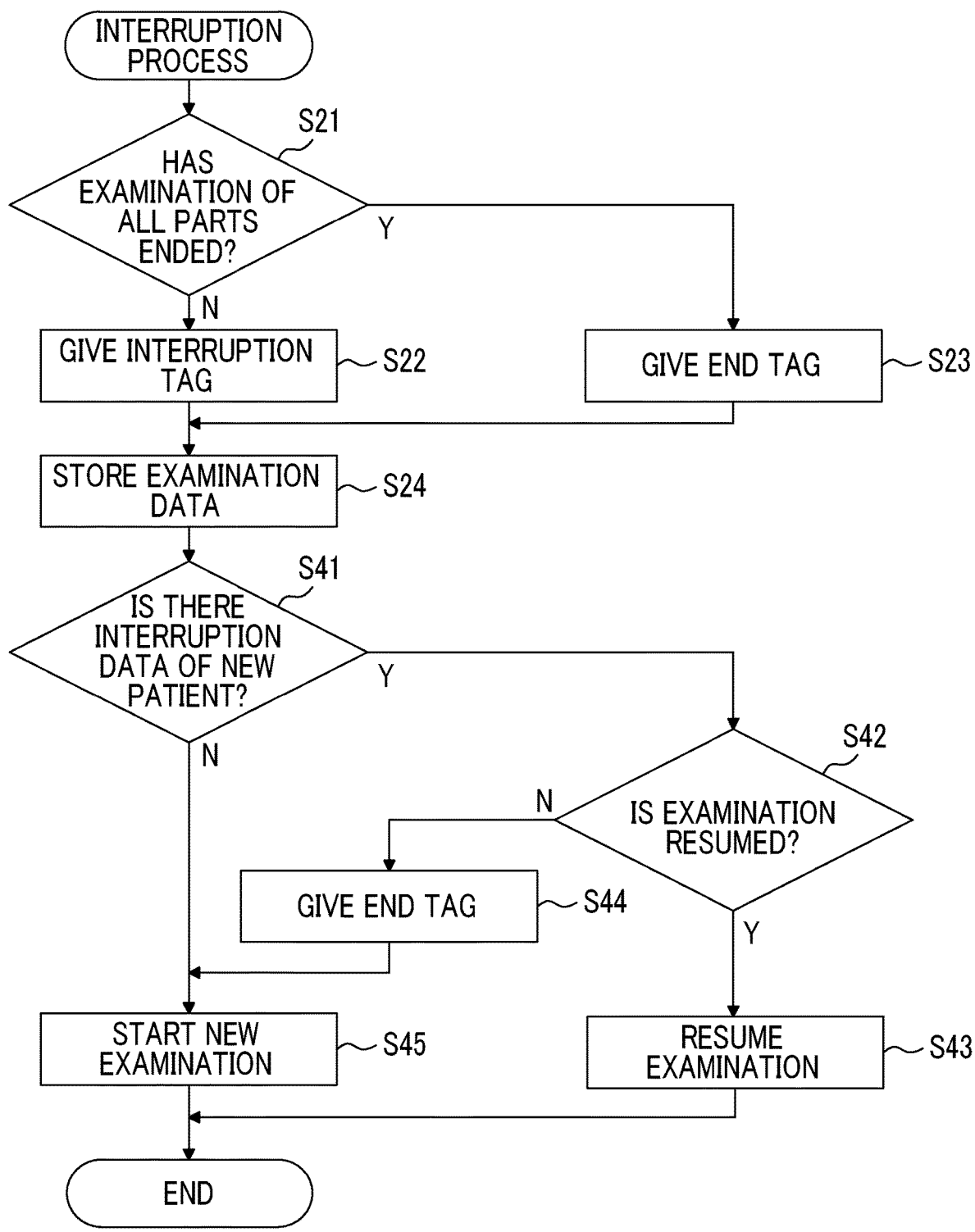
FIG. 10 is a flowchart illustrating an interruption process according to Embodiment 2.

Next, an interruption process according to Embodiment 2 will be described with reference to a flowchart illustrated in FIG. 10.

In a case in which new patient information (patient specification information) different from the patient information (patient specification information) of the patient who is currently being examined is input to the input unit 16 by an operation of the user, the examination data of the patient who is currently being examined is stored as examination interruption data or examination end data in the memory unit 15 through the process from Step S21 to Step S24.

Then, in Step S41, it is determined whether the examination interruption data associated with the new patient information (patient specification information) input to the input unit 16 has been stored in the memory unit 15. Specifically, the examination resumption determination unit 31 that has received the determination result of the examination situation determination unit 13 searches for the examination interruption data associated with the new patient information (patient specification information). The examination interruption data associated with the new patient information (patient specification information) stored in the memory unit 15 indicates that the examination of the patient corresponding to the new patient information (patient specification information) was interrupted in the past.

In addition, the examination interruption tag given to the new patient information (patient specification information) indicates that the examination of the patient corresponding to the new patient information (patient specification information) was interrupted in the past. In a case in which the examination interruption tag has not been given to the new patient information (patient specification information), it is considered that the examination of the patient corresponding to the new patient information (patient specification information) has not been interrupted and the examination interruption data has not been stored in the memory unit 15. In this case, the examination resumption determination unit 31 does not search for the examination interruption data associated with the new patient information (patient specification information) and determines that the examination interruption data associated with the new patient information (patient specification information) has not been stored in the memory unit 15.

In a case in which it is determined in Step S41 that the examination interruption tag has not been given to the new patient information (patient specification information) or the examination interruption data associated with the new patient information (patient specification information) has not been stored in the memory unit 15, the examination resumption determination unit 31 outputs the determination result to the apparatus control unit 12. Then, in Step S45, a new examination of the patient corresponding to the new patient information (patient specification information) starts.

On the other hand, in a case in which it is determined in Step S41 that the examination interruption data associated with the new patient information (patient specification information) has been stored in the memory unit 15, the examination resumption determination unit 31 outputs the determination result to the apparatus control unit 12. Then, in Step S42, it is determined whether to resume the interrupted examination. Specifically, the apparatus control unit 12 controls the display control unit 4 on the basis of the determination result of the examination resumption determination unit 31 such that a dialogue for allowing the user to determine whether to resume the interrupted examination is displayed on the display unit 5.

In a case in which the user determines to resume the examination in Step S42, the interrupted examination of the patient corresponding to the new patient information (patient specification information) is resumed in Step S43. In this case, since the content of the interrupted examination has already been associated with the new patient information (patient specification information), the examination is resumed for the content of the examination associated with the new patient information (patient specification information). For example, in a case in which the eFAST examination has been interrupted, the apparatus control unit 12 reflects the situation of the interrupted examination in the dialogue D illustrated in FIG. 5 on the basis of the examination interruption data. Therefore, the user can resume the examination with reference to the dialogue D in which the situation of the interrupted examination has been reflected.

In addition, in a case in which the user resumes the interrupted examination, the user may use all of the examination interruption data associated with the new patient information (patient specification information) or may use a portion of the examination interruption data. That is, a portion of the examination data obtained by the resumed examination can be replaced with a portion of the examination interruption data.

In a case in which the user determines not to resume the examination in Step S42, the examination resumption determination unit 31 outputs the determination result to the tag giving unit 14. Then, in Step S44, the tag giving unit 14 that has received the determination result of the examination resumption determination unit 31 gives the examination end tag to the examination interruption data associated with the new patient information (patient specification information). Then, the apparatus control unit 12 stores the examination interruption data, to which the examination end tag has been given, as the examination end data in the memory unit 15. Therefore, in a case in which the patient corresponding to the new patient information (patient specification information) is separately examined, the examination resumption determination unit 31 is prevented from determining that the examination interruption data associated with the new patient information (patient specification information) has been stored in the memory unit 15.

Then, in Step S45, a new examination of the patient corresponding to the new patient information (patient specification information) starts.

As such, in a case in which the examination interruption data associated with the new patient information (patient specification information) has been stored in the memory unit 15, it is possible to resume the interrupted examination with the examination interruption data.

In a case in which it is determined in Step S41 that the examination interruption data associated with the new patient information (patient specification information) has been stored in the memory unit 15, in Step S42, the user may start an examination, without determining whether to resume the examination, and may determine whether the examination has been resumed on the basis of examination data acquired by the resumed examination.

For example, in a case in which the B-mode image signals of the right abdomen and the left abdomen are included in the examination interruption data stored due to the interruption of the eFAST examination, if a B-mode image signal of the bladder is generated in the examination that has started, it is considered that the bladder to be examined after the left abdomen in the eFAST examination is examined. In a case in which the B-mode image of the bladder is generated in the examination that has started, it can be determined that the examination has been resumed.

In contrast, in a case in which a B-mode image signal of the right abdomen is generated in the examination that has started, it is considered that the right abdomen which has been examined is reexamined. In a case in which the B-mode image signal of the right abdomen is generated in the examination that has started, it can be determined that a new examination has started.

In this embodiment, the interruption process is performed in a case in which new patient information (patient specification information) different from the patient information (patient specification information) of the patient who is currently being examined is input to the input unit 16. However, the invention is not limited thereto. For example, the user may operate the input unit 16 to interrupt the examination of the patient who is currently being examined, without inputting new patient information (patient specification information), and may examine a patient different the patient. In this case, since no patient information (patient specification information) is input to the input unit 16, it is difficult to determine whether examination interruption data associated with the patient information (patient specification information) has been stored in the memory unit 15. Therefore, a new examination of the patient is regarded as having started. In a case in which patient information (patient specification information) is issued in parallel to the examination of the patient, the user knows that the patient information (patient specification information) has been present from information such as the name of the patient. In addition, in a case in which the examination interruption data associated with the patient information (patient specification information) has been stored in the memory unit 15, the user can read the examination interruption data and can determine whether to resume the examination.

With this configuration, it is possible to omit the input of the patient information (patient specification information) and to rapidly start an examination. In addition, in a case in which the examination interruption data has been stored in the memory unit 15, it is possible to resume the examination with the examination interruption data and thus to rapidly end the examination.

Embodiment 3

In Embodiment 2, in a case in which the examination resumption determination unit 31 determines that examination interruption data associated with new patient information (patient specification information) has been stored in the memory unit 15, the user determines to resume the interrupted examination. However, in Embodiment 3, the examination resumption determination unit 31 automatically determines whether to resume the examination.

Figure 11:
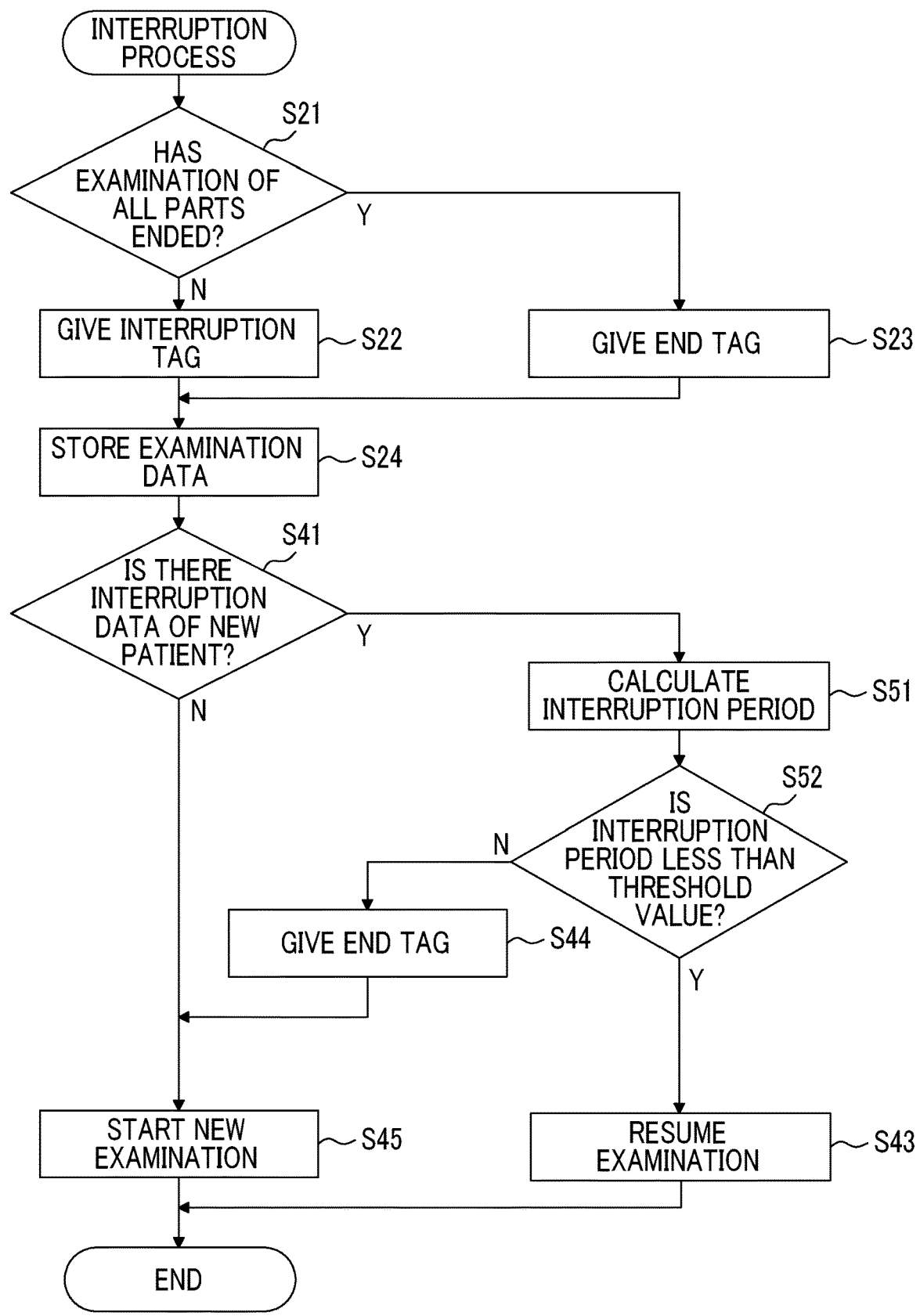
FIG. 11 is a flowchart illustrating an interruption process according to Embodiment 3.

An interruption process according to Embodiment 3 will be described with reference to a flowchart illustrated in FIG. 11.

In a case in which new patient information (patient specification information) different from the patient information (patient specification information) of the patient who is currently being examined is input to the input unit 16 by an operation of the user, the examination data of the patient who is currently being examined is stored in the memory unit 15 through the process from Step S21 to Step S24. Then, in Step S41, the examination resumption determination unit 31 that has received the determination result of the examination situation determination unit 13 determines whether the examination interruption data associated with the new patient information (patient specification information) input to the input unit 16 has been stored in the memory unit 15.

In a case in which it is determined in Step S41 that the examination interruption data associated with the new patient information (patient specification information) has been stored in the memory unit 15, the examination resumption determination unit 31 calculates an examination interruption period in Step S51.

Here, the examination interruption period is a period from the time when the tag giving unit 14 gives the examination interruption tag to the patient information (patient specification information) to the time when the patient information (patient specification information) is input to the input unit 16 again, that is, a period for which the examination of the patient corresponding to the patient information (patient specification information) is interrupted.

Then, in Step S52, it is determined whether the examination interruption period calculated by the examination resumption determination unit 31 is less than a preset threshold value. The threshold value of the examination interruption period can be set to, for example, 30 days. However, the threshold value may be appropriately changed.

In a case in which it is determined in Step S52 that the examination interruption period is less than the threshold value, the interrupted examination of the patient corresponding to the new patient information (patient specification information) is resumed in Step S43. In this case, the apparatus control unit 12 reflects the situation of the interrupted examination in the dialogue D on the basis of the examination interruption data. Therefore, after inputting new patient information (patient specification information) to the input unit 16, the user can resume the examination with reference to the dialogue D in which the situation of the interrupted examination has been reflected, without operating the input unit 16 at all.

On the other hand, in a case in which it is determined in Step S52 that the examination interruption period is equal to or greater than the threshold value, the examination resumption determination unit 31 outputs the determination result indicating that the interrupted examination is not resumed to the tag giving unit 14. The reason is as follows. In a case in which the examination interruption period is equal to or greater than the preset threshold value, the examination interruption data stored in the memory unit 15 is too old. It is considered that the use of the examination interruption data at the time of the resumption of the interrupted examination is inappropriate.

Then, in Step S44, the tag giving unit 14 gives the examination end tag to the examination interruption data associated with the new patient information (patient specification information). Then, the apparatus control unit 12 stores the examination interruption data, to which the examination end tag has been given, as the examination end data in the memory unit 15. In Step S45, a new examination of the patient corresponding to the new patient information (patient specification information) starts.

As such, in a case in which the examination interruption data associated with new patient information (patient specification information) has been stored in the memory unit 15, the examination interruption period is calculated and is compared with the preset threshold value. Therefore, it is possible to automatically determine whether to resume the interrupted examination.

In the resumed examination, for example, in a case in which the examination interruption data includes a B-mode image signal of the right abdomen, a dialogue may be displayed on the display unit 5 such that the user determines whether to overwrite a B-mode image signal obtained by newly examining the right abdomen on the B-mode image signal in the examination interruption data. In this case, the user can determine whether to resume the examination using all of the read examination interruption data, using some of the read examination interruption data, or without using the read examination interruption data.

EXPLANATION OF REFERENCES

1: ultrasound probe
1A: array transducer
2: transmitting/receiving unit
3: image generation unit
4: display control unit
5: display unit
6: transmitting unit
7: receiving unit
8: transmitting/receiving unit
9: B-mode processing unit
10: DSC
11: part determination unit
12: apparatus control unit
13: examination situation determination unit
14: tag giving unit
15: memory unit
16: input unit
17: storage unit
18: amplification unit
19: A/D conversion unit
20: beam former
21: signal processing unit
31: examination resumption determination unit
D: dialogue
T: text box
L: situation display portion
B: blank
S: schema image

What is claimed is:

1. An ultrasound diagnostic apparatus comprising:
an ultrasound probe;
an input device that is used by a user to input patient information including information for specifying a patient;
an examination content memory that stores content of an examination for continuously examining a plurality of examination parts of the patient associated with the patient information, the plurality of examination parts being located at positions separated from each other; and
a processor configured to:
transmit and receive an ultrasound beam to and from a patient using the ultrasound probe and convert a received signal output from the ultrasound probe into an image to generate an ultrasound image of an imaging part of the patient;
generate examination data including at least one ultrasound image generated by continuously examining the plurality of examination parts to store the generated examination data in the examination content memory;

determine, in a case in which new patient information is input to the input device during the continuous examination, whether the examination of all of the plurality of examination parts related to the content of the examination associated with the patient information has ended; and give an examination interruption tag indicating that an examination has been interrupted to the patient information in a case in which it is determined that the examination of all of the plurality of examination parts related to the content of the examination associated with the patient information has not ended and give an examination end tag indicating that an examination has ended to the patient information in a case in which it is determined that the examination of all of the plurality of examination parts related to the content of the examination associated with the patient information has ended.

2. The ultrasound diagnostic apparatus according to claim 1, wherein the processor is further configured to store the content of the examination in the examination content memory so as to be associated with the patient information.

3. The ultrasound diagnostic apparatus according to claim 2, wherein the processor is further configured to give the examination interruption tag to the examination data in a case in which it is determined that the examination of all of the plurality of examination parts related to the content of the examination associated with the patient information has not ended and give the examination end tag to the examination data in a case in which it is determined that the examination of all of the plurality of examination parts related to the content of the examination associated with the patient information has ended, and store the examination data, to which the examination interruption tag has been given by the tag giving unit, as examination interruption data in the examination content memory unit so as to be associated with the patient information in a case in which it is determined that the examination of all of the plurality of examination parts related to the content of the examination associated with the patient information has not ended and store the examination data, to which the examination end tag has been given by the tag giving unit, as examination end data in the examination content memory so as to be associated with the patient information in a case in which it is determined that the examination of all of the plurality of examination parts related to the content of the examination associated with the patient information has ended.

4. The ultrasound diagnostic apparatus according to claim 3, wherein the processor is further configured to store the examination data, from which the ultrasound image that is not suitable for diagnosis has been removed, in the examination content memory according to a result of the determination whether the examination of all of the plurality of examination parts related to the content of the examination associated with the patient information has ended.

5. The ultrasound diagnostic apparatus according to claim 3, wherein the processor is further configure to determine whether the examination interruption data associated with the new patient information has been stored in the examination content memory, determine whether to resume the interrupted continuous examination in a case in which it is determined that the examination interruption data associated with the new patient information has been stored in the examination content memory, and determine to start a new continuous examination in a case in which the interrupted continuous examination is not resumed.

6. The ultrasound diagnostic apparatus according to claim 5, wherein the processor is further configured to store the examination data, from which the ultrasound image that is not suitable for diagnosis has been removed, in the examination content memory according to a result of the determination whether the examination of all of the plurality of examination parts related to the content of the examination associated with the patient information has ended.

7. The ultrasound diagnostic apparatus according to claim 5, wherein the processor is further configured to determine to resume the interrupted continuous examination in a case in which an examination interruption period from a time when the examination interruption tag is given to the new patient information to a time when the new patient information is input to the input device again is less than a preset threshold value and determine to start a new continuous examination in a case in which the examination interruption period is equal to or greater than the preset threshold value.

8. The ultrasound diagnostic apparatus according to claim 7, wherein the processor is further configured to store the examination data, from which the ultrasound image that is not suitable for diagnosis has been removed, in the examination content memory according to a result of the determination whether the examination of all of the plurality of examination parts related to the content of the examination associated with the patient information has ended.

9. The ultrasound diagnostic apparatus according to claim 5, wherein the processor is further configured to give the examination end tag to the examination interruption data associated with the new patient information in a case in which it is determined to start the new continuous examination, and store the examination interruption data, to which the examination end tag has been given by the tag giving unit, as the examination end data in the examination content memory.

10. The ultrasound diagnostic apparatus according to claim 9, wherein the processor is further configured to determine to resume the interrupted continuous examination in a case in which an examination interruption period from a time when the examination interruption tag is given to the new patient information to a time when the new patient information is input to the input device again is less than a preset threshold value and determine to start a new continuous examination in a case in which the examination interruption period is equal to or greater than the preset threshold value.

11. The ultrasound diagnostic apparatus according to claim 10,
wherein the processor is further configured to store the examination data, from which the ultrasound image that is not suitable for diagnosis has been removed, in the examination content memory according to a result of the determination whether the examination of all of the plurality of examination parts related to the content of the examination associated with the patient information has ended.

12. The ultrasound diagnostic apparatus according to claim 9,
wherein the processor is further configured to store the examination data, from which the ultrasound image that is not suitable for diagnosis has been removed, in the examination content memory according to a result of the determination whether the examination of all of the plurality of examination parts related to the content of the examination associated with the patient information has ended.

13. The ultrasound diagnostic apparatus according to claim 1,
wherein the processor is further configured to determine the imaging part of the patient on the basis of the ultrasound image generated, and
determine whether the examination of all of the plurality of examination parts related to the content of the examination associated with the patient information has ended on the basis of a result of the determination of the imaging part.

14. The ultrasound diagnostic apparatus according to claim 13,
wherein the processor is further configured to give the examination interruption tag to the examination data in a case in which it is determined that the examination of all of the plurality of examination parts related to the content of the examination associated with the patient information has not ended and give the examination end tag to the examination data in a case in which it is determined that the examination of all of the plurality of examination parts related to the content of the examination associated with the patient information has ended, and
store the examination data, to which the examination interruption tag has been given by the tag giving unit, as examination interruption data in the examination content memory so as to be associated with the patient information in a case in which it is determined that the examination of all of the plurality of examination parts related to the content of the examination associated with the patient information has not ended and store the examination data, to which the examination end tag has been given by the tag giving unit, as examination end data in the examination content memory so as to be associated with the patient information in a case in which it is determined that the examination of all of the plurality of examination parts related to the content of the examination associated with the patient information has ended.

15. The ultrasound diagnostic apparatus according to claim 14, wherein
the processor is further configured to determine whether the examination interruption data associated with the new patient information has been stored in the examination content memory, determine whether to resume the interrupted continuous examination in a case in which it is determined that the examination interruption data associated with the new patient information has been stored in the examination content memory, and determine to start a new continuous examination in a case in which the interrupted continuous examination is not resumed.

16. The ultrasound diagnostic apparatus according to claim 15,
wherein the processor is further configured to give the examination end tag to the examination interruption data associated with the new patient information in a case in which it is determined to start the new continuous examination, and
store the examination interruption data, to which the examination end tag has been given by the tag giving unit, as the examination end data in the examination content memory.

17. The ultrasound diagnostic apparatus according to claim 16,
wherein the processor is further configured to determine to resume the interrupted continuous examination in a case in which an examination interruption period from a time when the examination interruption tag is given to the new patient information to a time when the new patient information is input to the input device again is less than a preset threshold value and determine to start a new continuous examination in a case in which the examination interruption period is equal to or greater than the preset threshold value.

18. The ultrasound diagnostic apparatus according to claim 15,
wherein the processor is further configured to determine to resume the interrupted continuous examination in a case in which an examination interruption period from a time when the examination interruption tag is given to the new patient information to a time when the new patient information is input to the input device again is less than a preset threshold value and determine to start a new continuous examination in a case in which the examination interruption period is equal to or greater than the preset threshold value.

19. A method for controlling an ultrasound diagnostic apparatus, the method comprising:
a step of transmitting and receiving an ultrasound beam to and from a patient using an ultrasound probe and converting a received signal output from the ultrasound probe into an image to generate an ultrasound image of an imaging part of the patient;
a step of allowing a user to input patient information including information for specifying a patient;
a step of storing content of an examination for continuously examining a plurality of examination parts of the patient so as to be associated with the patient information, the plurality of examination parts being located at positions separated from each other;
a step of, in a case in which new patient information is input during the continuous examination, determining whether the examination of all of the plurality of examination parts related to the content of the examination associated with the patient information has ended; and
a step of giving an examination interruption tag indicating that an examination has been interrupted to the patient information in a case in which it is determined that the examination of all of the plurality of examination parts related to the content of the examination associated with the patient information has not ended and giving an examination end tag indicating that an examination has ended to the patient information in a case in which it is determined that the examination of all of the plurality of examination parts related to the content of the examination associated with the patient information has ended.

\* \* \* \* \*